United States Patent [19]

Scarpelli et al.

[11] Patent Number: 5,043,161

[45] Date of Patent: Aug. 27, 1991

[54] SMALL, OILY, FREE-FLOWING, SILKY-SMOOTH, TALC-LIKE, DRY MICROCAPSULES AND AQUEOUS FORMULATIONS CONTAINING THEM

[75] Inventors: Joseph A. Scarpelli, Dayton; Jon C. Soper, Huber Heights, both of Ohio

[73] Assignee: Eurand America, Inc., Vandalia, Ohio

[21] Appl. No.: 401,422

[22] Filed: Aug. 31, 1989

[51] Int. Cl.$^5$ .......................... A61K 7/00; A61K 9/14
[52] U.S. Cl. ........................... 424/401; 424/59; 424/63; 424/69; 424/70; 424/489; 424/502; 514/844
[58] Field of Search ................ 424/63, 64, 401, 489

[56] References Cited

U.S. PATENT DOCUMENTS

| | | | |
|---|---|---|---|
| 3,965,033 | 6/1976 | Matsukawa et al. | 424/493 |
| 3,978,204 | 8/1976 | Charlé et al. | 424/401 |
| 4,115,315 | 9/1978 | Marinelli | 424/70 |
| 4,394,287 | 7/1983 | Scarpelli | 424/494 |
| 4,879,175 | 11/1989 | Ugro, Jr. | 424/63 |

Primary Examiner—Thurman K. Page
Assistant Examiner—James M. Spear
Attorney, Agent, or Firm—Gary R. Molnar

[57] ABSTRACT

This disclosure is directed to the preparation of dry microencapsulated product, having an oily core material with microcapsule cell wall materials having a first cell wall of gelatin/polyvinyl methylether maleic anhydride copolymer (PVMMA)/carboxymethylcellulose (CMC) which is prehardened (cross-linked) with a material selected from the group consisting of formaldehyde, glyoxal and glutaraldehyde to which there is grafted formaldehyde and resorcinol which is then crosslinked with formaldehyde and urea, and aqueous formulations containing them. Approximately 97% of these microcapsules have a size less than 100 and more characteristically having a particle size peak distribution of 30 to 40 microns (microcapsular diameter). These microcapsules contain less than approximately 3 wt. % free oil and more characteristically less than about 1 wt. % free oil (non-micro-encapsulated oil) and have less free (unreacted) formaldehyde which can be extracted with water, than do prior art microencapsulated emollient materials. The dry microcapsules of this invention are free-flowing and have a silky-smooth feeling similar to that of talcum powder.

13 Claims, No Drawings

SMALL, OILY, FREE-FLOWING, SILKY-SMOOTH, TALC-LIKE, DRY MICROCAPSULES AND AQUEOUS FORMULATIONS CONTAINING THEM

BRIEF DESCRIPTION OF THE INVENTION

This invention is directed to the preparation of dry microencapsulated product, having an oily core material with microcapsule cell wall materials having a first cell wall of gelatin/polyvinyl methylether maleic anhydride copolymer (PVMMA)/carboxymethylcellulose (CMC) which is prehardened (cross-linked) with a material selected from the group consisting of formaldehyde, glyoxal and glutaraldehyde to which there is grafted formaldehyde and resorcinol which is then crosslinked with formaldehyde and urea, and aqueous formulations containing them. Approximately 97% of these microcapsules have a size less than 100 and more characteristically have a particle size peak distribution of 30 to 40 microns (microcapsular diameter). These microcapsules contain less than approximately 3 wt. % free oil and more characteristically less than about 1 wt. % free oil (non-microencapsulated oil) and have less free (unreacted) formaldehyde which can be extracted with water, than do prior art microencapsulated emollient materials. The dry microcapsules of this invention are free-flowing and have a silky-smooth feeling similar to that of talcum powder.

BACKGROUND OF THE INVENTION AND PRIOR ART

There long has been a desire in the cosmetic industry for a dry aesthetically pleasing cosmetic product which has a silky-smooth feeling (similar to talc) when applied to the skin, and is substantially non-toxic, is free flowing, and has a small particle size to constitute a dry cosmetic product which can be applied to the skin.

There have been various attempts in the prior art to arrive at such a cosmetically desired product. For example, the 3M Company in its encapsulated products/3M Product Information Bulletin, entitled "3M Microcapsules Mineral Oil/180 Microns" bearing a number of 77-9802-7051-4 describes a micro-encapsulated mineral oil, which microcapsules are reported to have a diameter of 180 microns and are described as soft clumps of grainy, white powder with a slightly grainy feel. The microencapsulated core material is USP grade mineral oil and when pressure is applied the microcapsules break and mineral oil is released. This product has clumps or agglomerates of individual microcapsules and is stated to contain a maximum of 12 weight percent of free (non-microencapsulated) mineral oil. This product also contains 400 parts per million (maximum) of aqueous extractable formaldehyde. This product bulletin also includes the further designation of "Resin FDA CRNCS No. R0012291". The microencapsulating cell wall material, or shell material, is a urea-formaldehyde resin. The material corresponding to this 3M Product Information Bulletin does not have the free-flowing, smooth feeling, talc-like characteristics of the microcapsules produced in accordance with this invention.

R. W. Baker U.S. Pat. No. 4,808,408, is directed to preparation of microencapsulated hydrophobic materials, including fragrances. Also there is disclosed in Example 5 use of a "Gantrez" resin as a pharmaceutical vehicle to produce a resulting cream containing insect repellent.

S. Egawa U.S. Pat. No. 4,082,688, is directed to a process for producing microcapsules having a gelatin cell wall material wherein the microcapsule wall is produced by coacervation and hardened using at least two kinds of chemical hardening agents in a hardening step(s).

R. Charle et al U.S. Pat. No. 3,691,270, is directed to microencapsulation of make-up removing or treating compositions which are incorporated into a cosmetic cream or incorporated in a flexible support described as an aloe vera polymer support.

H. G. Monismer U.S. Pat. No. 4,205,060, teaches in its Example 5 use of hydrolyzed "Gantrez AN169" copolymer of methyl vinyl ether and maleic anhydride to microencapsulate medicaments.

It will be clearly evident that the dry lubricant microcapsules of the present invention possess a desirable combination of properties not possessed by the prior art patents and the product bulletin referred to above.

DETAILED DESCRIPTION OF THE INVENTION

The dry microcapsules of the present invention are characterized as (1) even coating when applied to the skin, (2) having a silky-smooth feeling similar to that of talcum powder, (3) being free-flowing and (4) having a smaller effective particle size, due to the substantial absence of agglomerates and clumps, than available prior art microencapsulated emollients in that the microencapsulated dry lubricant oils of this invention are about 97% by weight having a particle size of less than 100 microns and more characteristically have a particle size peak distribution of 30 to 40 microns (microcapsule diameter). Moreover, these dry oily core microcapsules (5) contain a maximum of approximately 3 wt. % free oil and more characteristically less than about 1 wt. % free (non-microencapsulated) oil and (6) contain less free formaldehyde, viz., that which can be extracted with water, than prior art emollients.

The analytical procedure used for free oil analysis is not capable of determining free oil with highly volatile microcapsule core materials, such as fragrance oils.

A variety of core materials can be employed to form the microcapsules in accordance with the present invention. Suitable core materials of an oily nature which can be employed in the present invention include, but are not necessarily limited to, the following: mineral oil, and other lubricant oils, emollients, fragrance oils, escalol and other oily sunscreen materials, aloe vera, silicone oil, jojoba oil, esters of vitamin E, such as vitamin E acetate, vitamin E linoleate, vitamin E palmitate, vitamin A, menthol eucalyptus formulations, fruit oils, e.g., lemon oil, citrus fragrance oil, and other citrus base fragrances, oily color producing materials, etc.

The microencapsulating cell wall materials employed in accordance with this invention result in what is believed to be a basic microcapsule cell wall of gelatin/polyvinyl methylether maleic anhydride copolymer (PVMMA)/carboxymethylcellulose (CMC) prehardened with a material selected from the group consisting of formaldehyde, glyoxal and glutaraldehyde and grafted with formaldehyde and resorcinol and cross linked with formaldehyde and urea. Whether this results (A) in two separate and discrete microcapsule walls, the interior one being the gelatin/PVMMA/CMC polymer and the outer microcapsular cell wall being the resorcinol-formaldehyde/urea formaldehyde resin, or (B) in one microcapsular wall of mixed composition is not clearly understood.

It is believed, however, that the resorcinol-formaldehyde/urea formaldehyde polymer forming components of the cell wall(s) react(s) with the gelatin/PVMMA/CMC cell wall previously formed and prevents the weeping of the oily core material therefrom while strengthening the initially formed microcapsule gelatin/PVMMA/CMC wall and makes it sufficiently strong to withstand the rigors of processing, such as washing, drying, sieving and packaging. Also, it is believed that the resorcinol, formaldehyde/urea, formaldehyde polymer form a complex with the hydrophilic groups on the gelatin-containing initially formed polymer cell wall and shrink it while hardening same thereby enabling the aesthetically desired small microcapsule size to be obtained in conjunction with the very low concentration of free oily core material while avoiding the formation of agglomerates or clumps of microcapsules such as is encountered in some prior art products. The present invention is not dependent for successful operation on this or any other theory however.

The present invention will be illustrated in greater detail in the examples which follow:

EXAMPLE 1

(Microencapsulation of mineral oil "Blandol" to produce a dry lubricant microencapsulated emollient)

200 grams of 10% weight percent aqueous gelatin solution at 40 degrees C. are combined with 600 grams of distilled water at 40 degrees C. in a mixing tank. Then 200 grams of the internal phase core material "Blandol" mineral oil are milled into the gelatin/water previously added to produce the desired particle size core material, e.g., 5 to 50 microns, and the pH of this mix is adjusted with a 20 weight % aqueous sodium hydroxide to a pH of 6.5 to 7.0.

Then there is added 55 cc of a two percent by weight aqueous solution containing equal weight parts of "Gantrez resin No. AN119, AN139" and "Aqualon CMC7LF". This solution is adjusted to a pH of 7 prior to addition.

Then the preparation is cooled slowly to a temperature of 28 degrees C. followed by a fast cooling to 20 degrees C. The pH of this preparation is then adjusted to a pH of 5.5 at 20 degrees C. using 10% by weight aqueous acetic acid solution for pH adjustment. The preparation is then prehardened using 5 cc's of a 25 weight percent aqueous solution of glutaraldehyde.

POST TREATMENT

After permitting the preparation to stand for 2-3 hours, there is added thereto a polyvinyl alcohol solution consisting of 5 weight percent aqueous solution of duPont "Evanol 71/30" in an amount of 12 cc's.

This preparation is then stirred for 10 minutes and the pH thereof is adjusted to 3 with a 10% by weight aqueous sulfuric acid solution using approximately 10-12 ml thereof for this purpose. After stirring said preparation for 5 minutes, 12.7 cc of a 37 weight percent aqueous formaldehyde solution is added. Then the preparation is stirred continuously for 5 minutes whereupon 11.2 grams of resorcinol predissolved in 20 cc of water is added to the preparation in a small amount of water.

Then the preparation is stirred for 1 hour whereupon 37.5 cc's of a 37 weight percent aqueous formaldehyde solution is added, following by stirring for 5 minutes. Then 18.8 grams of urea predissolved in 30 ml of water is added to the preparation. This preparation is then stirred for one hour, after which the pH is adjusted to 1.4 using a 10 weight percent aqueous solution of sulfuric acid. This preparation is then stirred from 6 to 16 hours. The microencapsulated mineral oil formulation is then washed twice with approximately equal volumes of water, followed by neutralization to a pH of 5.5 to 4.5 using 20 wt. % aqueous sodium hydroxide solution to accomplish this pH adjustment.

After this, the washed, neutralized microcapsules are Buchner filtered and dried using a fluidized bed dryer.

The resulting mineral oil microcapsules have a 97% particle size of less than 100 microns and, more characteristically, have a peak particle size distribution between 30 and 40 microns (microcapsule diameter). These microcapsules were then analyzed for free mineral oil and upon analysis 2.3 weight percent of free (non-microencapsulated) mineral oil was found to be present. The free formaldehyde present in these dried microcapsules was determined to be 254 parts per million by aqueous extraction.

These microcapsules have a light beige appearance which is aesthetically pleasing, and exhibit a smooth feeling (similar to talc) when placed upon the skin. They were observed to be free-flowing and substantially free from agglomeration or clumping.

EXAMPLE 2

(Microencapsulation of "Escalol" sunscreen oil to produce a dry lubricant microencapsulated sun screen)

200 grams of 10 wt. % aqueous gelatin solution at 40 degrees C. are combined with 600 grams of distilled water at 40 degrees C. in a mixing tank. Then 200 grams of the internal phase core material Escalol 507 and Escalol 557 (7:3 blend) at 50 degrees C. are milled into the gelatin/water solution to produce the desired particle size core material, i.e., 5 to 50 microns, and the pH of this mixture is adjusted with 20% aqueous sodium hydroxide solution to a pH of 6.5-7.0. Then there is added 55 cc of a two percent by weight aqueous solution containing equal weight parts of "Gantrez resin No. AN119, AN139" and "Aqualon CMC 7LF." This solution is adjusted to a pH of 7 prior to addition.

Then the preparation is cooled slowly to a temperature of 28 degrees C. followed by a fast cooling to 20 degrees C. The pH of this preparation is then adjusted to a pH of 5.5 at 20 degrees C. using a 10% aqueous solution of acetic acid for the adjustment. The preparation is then pre-hardened with glutaraldehyde treatment using 5 cc of a 25 weight percent aqueous solution.

This material is then post treated, as in Example 1, to yield free flowing, dry powder containing 0.74 wt. % of free (nonmicroencapsulated) escalol sun screen oil and 173 parts per million free formaldehyde by aqueous extraction.

EXAMPLE 3

(Microencapsulation of Citrus base fragrance oil to produce dry powder fragrance microcapsules)

200 grams of 10 wt. % aqueous gelatin solution at 40 degrees C. are combined with 600 grams of distilled water at 40 degrees C. in a mixing tank. Next, 200 grams of room temperature internal phase citrus base fragrance oil are milled into the gelatin/water solution to produce the desired particle size core material, i.e., 5-100 microns and the pH of this mixture is adjusted with 20% aqueous sodium hydroxide solution to a pH of 6.5-7.0. Then there is added 44 cc of a two percent, by weight, aqueous solution containing equal parts of Gantrez resin No. AN119, AN139 and Aqualon CMC 7LF. This solution is adjusted to a pH of 7 prior to addition.

Then the preparation is cooled slowly to a temperature of 28 degrees C. followed by a fast cool to 20 degrees C. The pH of the preparation is then adjusted to a pH of 5.5 at 20 degrees C. using a 10% aqueous acetic acid solution for the adjustment. The preparation is then pre-hardened with glutaraldehyde treatment using 5 cc of a 25 wt. % aqueous solution.

This material is than post treated as in Example 1 to yield free flowing, dry powder containing citrus base fragrance oil and having 139 parts per million free formaldehyde by aqueous extraction. The percent free fragrance oil could not be determined due to the high volatility of this core material.

EXAMPLE 4

(Microencapsulation of Mineral Oil "Blandol" to produce dry lubricant microcapsules of much lighter beige color than Example 1)

200 grams of 10 weight percent aqueous gelatin solution at 40 degrees C. are combined with 600 grams distilled water at 40 degrees C. in a mixing tank. Then 200 grams of the internal phase "Blandol" mineral oil are milled into the gelatin/water solution to produce the desired particle size core material, i.e. 5-50 microns, and the pH of this mix is adjusted with 20% aqueous sodium hydroxide solution to a pH of 6.5-7.0.

Then there is added 45 cc of a 2 percent by weight aqueous solution containing equal weight parts of Gantrez resin No. AN119, AN139 and Aqualon CMC 7LF. This solution is adjusted to a pH of 7 prior to addition.

Then the preparation is cooled slowly to a temperature of 28 degrees C. followed by a fast cooling to 10 degrees C. The preparation is then pre-hardened by adding 5 cc of formalin and 20 cc of a 5% Gantrez AN903 aqueous solution. This solution is adjusted to a pH of 9 prior to addition.

The batch is allowed to warm up to room temperature for one hour and then the pH raised to 9.0 by the addition of a 10% by weight aqueous solution of sodium hydroxide with continued stirring for one hour.

This material is then post treated as in Example 1 to yield a free flowing dry powder which although a light beige color is more white than the product of Example 1. This material contained 0.13 wt. % free mineral oil and 117 parts per million free formaldehyde by aqueous extraction.

Due to their free flowing nature and the substantial freedom from clumps and agglomerates of individual microcapsules, the oily core microcapsules of this invention having microcapsular cell wall material of gelatin polyvinylmethylether maleic anhydride copolymer/carboxymethylcellulose prehardened with a material selected from the group consisting of formaldehyde glyoxal and glutaraldehyde and having grated thereto formaldehyde and resorcinol and crosslinked with formaldehyde and urea and having approximately 97% by weight, having a particle size less than 100 microns are well suited to the preparation of aqueous formulations containing said microcapsules.

These aqueous formulations characteristically contain from about 10 to about 40 wt. % of said microcapsules with the remainder being water and formulation aids. Such aqueous formulations can be used to impregnate, coat or otherwise deliver said microcapsules to woven and non-woven fabric substrates; rubber, plastic and other polymer foam structures; paper, etc. These aqueous formulations can be made from the dried microcapsules or by tailor making them without drying by use of the desired amount of water.

The oily core microcapsules in such aqueous formulations characteristically have a particle size peak distribution of 30 to 40 microns.

We claim:

1. Aqueous formulations containing from about 10 to about 40 wt. % of individual, free flowing microcapsules, having a particle size less than 100 microns and being substantially free of clumps and agglomerates of individual microcapsules, containing oil in the core material and containing microcapsular cell wall material of gelatin/polyvinylmethylether maleic anhydride copolymer/carboxymethylcellulose prehardened with a material selected from the group consisting of formaldehyde, glyoxal and glutaraldehyde and having grafted thereto formaldehyde and resorcinol and crosslinked with formaldehyde and urea, with the remainder being water and formulation aids.

2. Microencapsulated product as in claim 1 wherein said oil in the core material contains emollient.

3. Microencapsulated product as in claim 1 wherein said oil in the material contains lubricant.

4. Microencapsulated product as in claim 1 wherein said oil in the core material contains mineral oil.

5. Microencapsulated product as in claim 1 wherein said oil in the core material contains fragrance oil.

6. Microencapsulated product as in claim 1 wherein said oil in the core material contains sunscreen.

7. Microencapsulated product as in claim 1 wherein said oil in the core material contains aloe vera.

8. A process of producing the microencapsulated dry product of claim 1 which comprises microencapsulating an oil in the core material with a microcapsule cell wall system of gelatin/polyvinyl methylether maleic anhydride/carboxymethylcellulose, prehardening same with a material selected from the group consisting of formaldehyde, glyoxal and glutaraldehyde and thereafter grafting to the initially formed microcapsule cell wall material formaldehyde and resorcinol and subsequently crosslinking with formaldehyde and urea.

9. Aqueous formulations as in claim 1 wherein said oil in the core material contains fragrance oil.

10. Aqueous formulations as in claim 1 wherein said oil in the core material contains color producing material.

11. Aqueous formulations as in claim 1 wherein said oil in the core material contains citrus base fragrance oil.

12. Aqueous formulations as in claim 1 wherein oil in the core material contains an emollient.

13. Aqueous formulations as in claim 1 wherein said microcapsules have a particle size peak distribution of 30 to 40 microns.

* * * * *